(12) United States Patent
Headley et al.

(10) Patent No.: US 7,947,070 B2
(45) Date of Patent: May 24, 2011

(54) DILATATION AND STENT DELIVERY SYSTEM AND RELATED METHODS

(75) Inventors: F. Anthony Headley, Marlborough, MA (US); Peter Shank, Boylston, MA (US); Emily Rusk, Watertown, MA (US); John Damarati, Marlborough, MA (US); Michael Abi-Kheirs, Weymouth, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1309 days.

(21) Appl. No.: 10/439,298

(22) Filed: May 16, 2003

(65) Prior Publication Data
US 2004/0230284 A1     Nov. 18, 2004

(51) Int. Cl.
*A61F 2/06* (2006.01)
*A61F 11/00* (2006.01)

(52) U.S. Cl. ...................................... 623/1.11; 606/108
(58) Field of Classification Search .................. 606/108, 606/191, 194, 195, 198; 623/1.11
See application file for complete search history.

(56) References Cited

U.S. PATENT DOCUMENTS

| 5,456,694 A | 10/1995 | Marin et al. | |
|---|---|---|---|
| 5,634,928 A * | 6/1997 | Fischell et al. | 623/1.11 |
| 5,749,890 A | 5/1998 | Shaknovich | |
| 5,807,398 A | 9/1998 | Shaknovich | |
| 5,810,871 A | 9/1998 | Tuckey et al. | |
| 6,174,327 B1 | 1/2001 | Mertens et al. | |
| 2003/0149467 A1* | 8/2003 | Linder et al. | 623/1.11 |
| 2003/0212431 A1* | 11/2003 | Brady et al. | 606/200 |

FOREIGN PATENT DOCUMENTS

| EP | 0 873 730 A2 | 10/1998 |
|---|---|---|
| WO | WO 97/07756 | 3/1997 |
| WO | WO 02/055124 A2 | 7/2002 |

* cited by examiner

*Primary Examiner* — Vy Q. Bui
(74) *Attorney, Agent, or Firm* — Vidas, Arrett & Steinkraus, P.A.

(57) ABSTRACT

The invention relates to a system for dilatation of a body passage and delivery of a stent into the body passage of a patient, and related methods of using such a system. The dilatation and stent delivery system may comprise a dilatation catheter having an expandable member on a distal end, and a stent delivery catheter configured to retain a stent and deliver the stent to a body passage. The stent delivery catheter defines a lumen sized to receive the dilatation catheter and permit movement of the dilatation catheter relative to the stent delivery catheter.

27 Claims, 6 Drawing Sheets

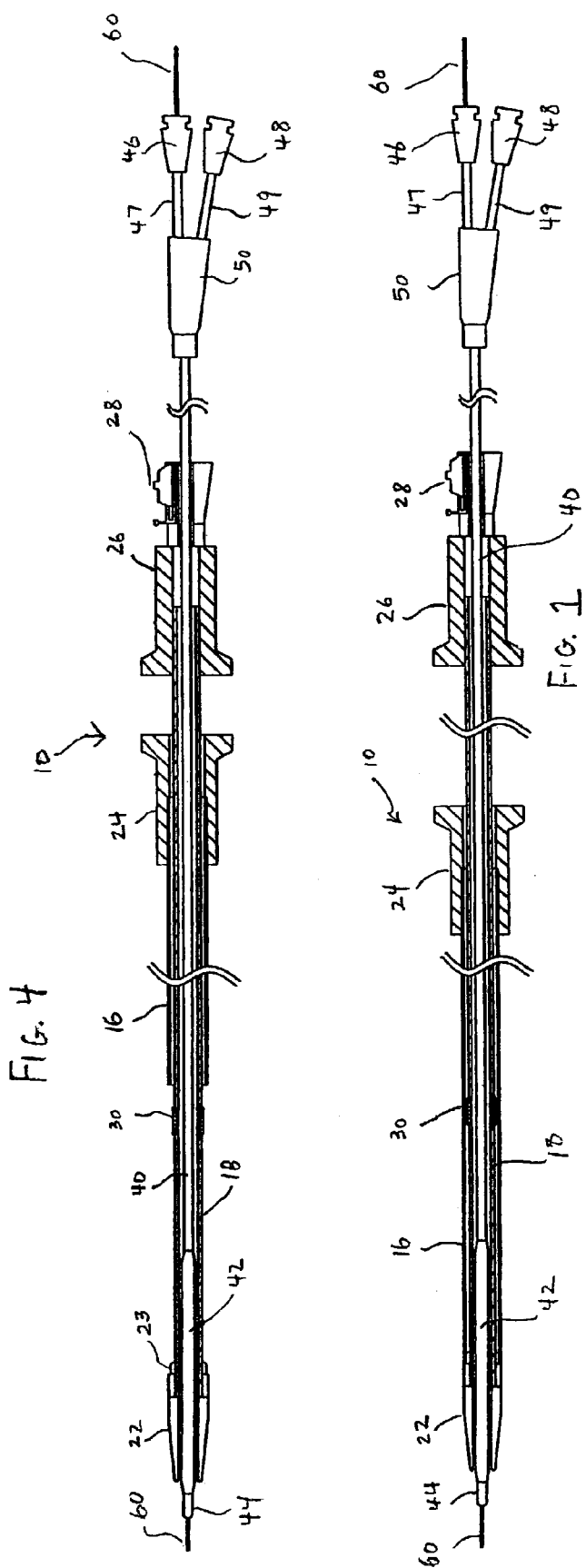

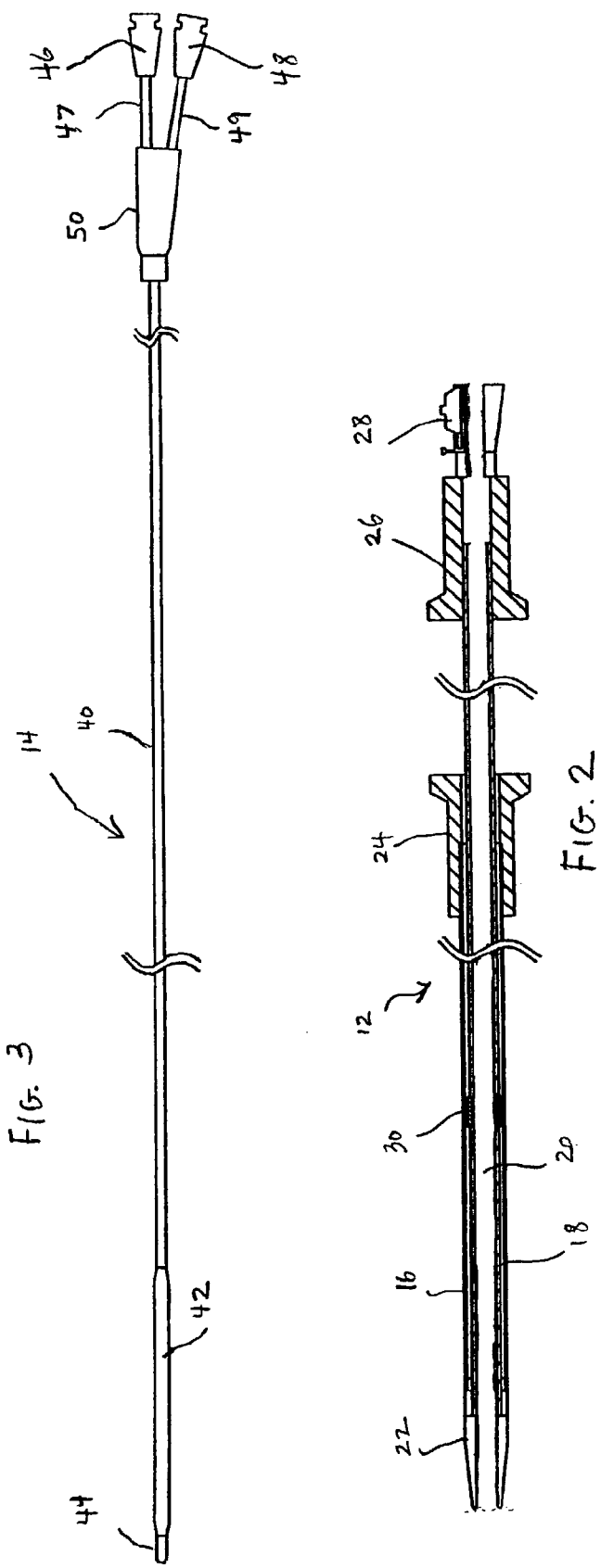

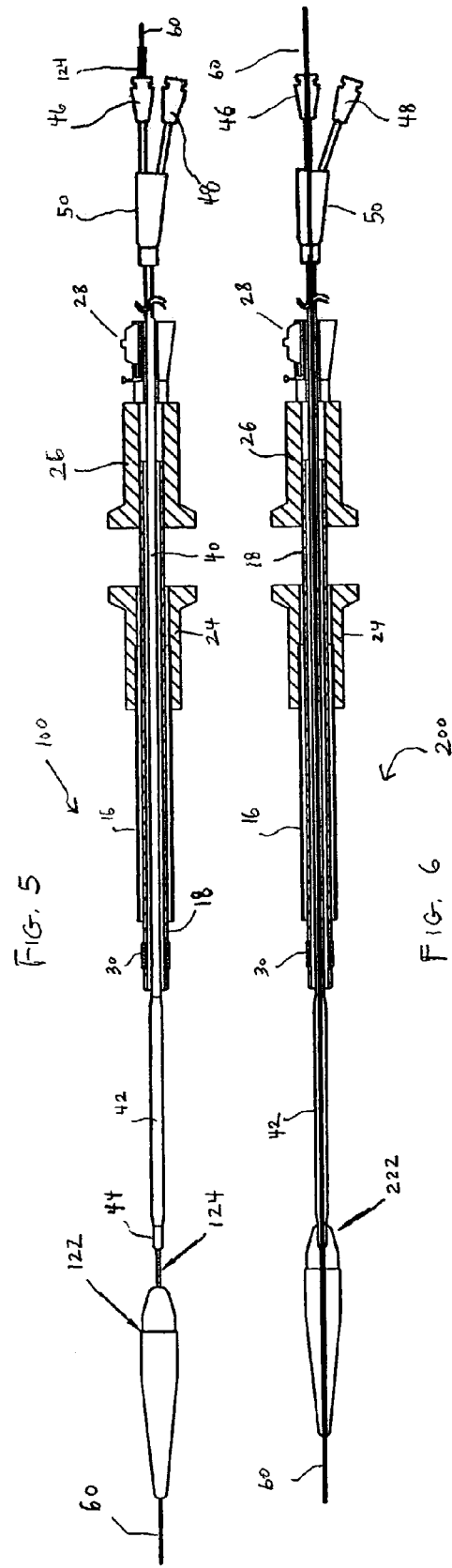

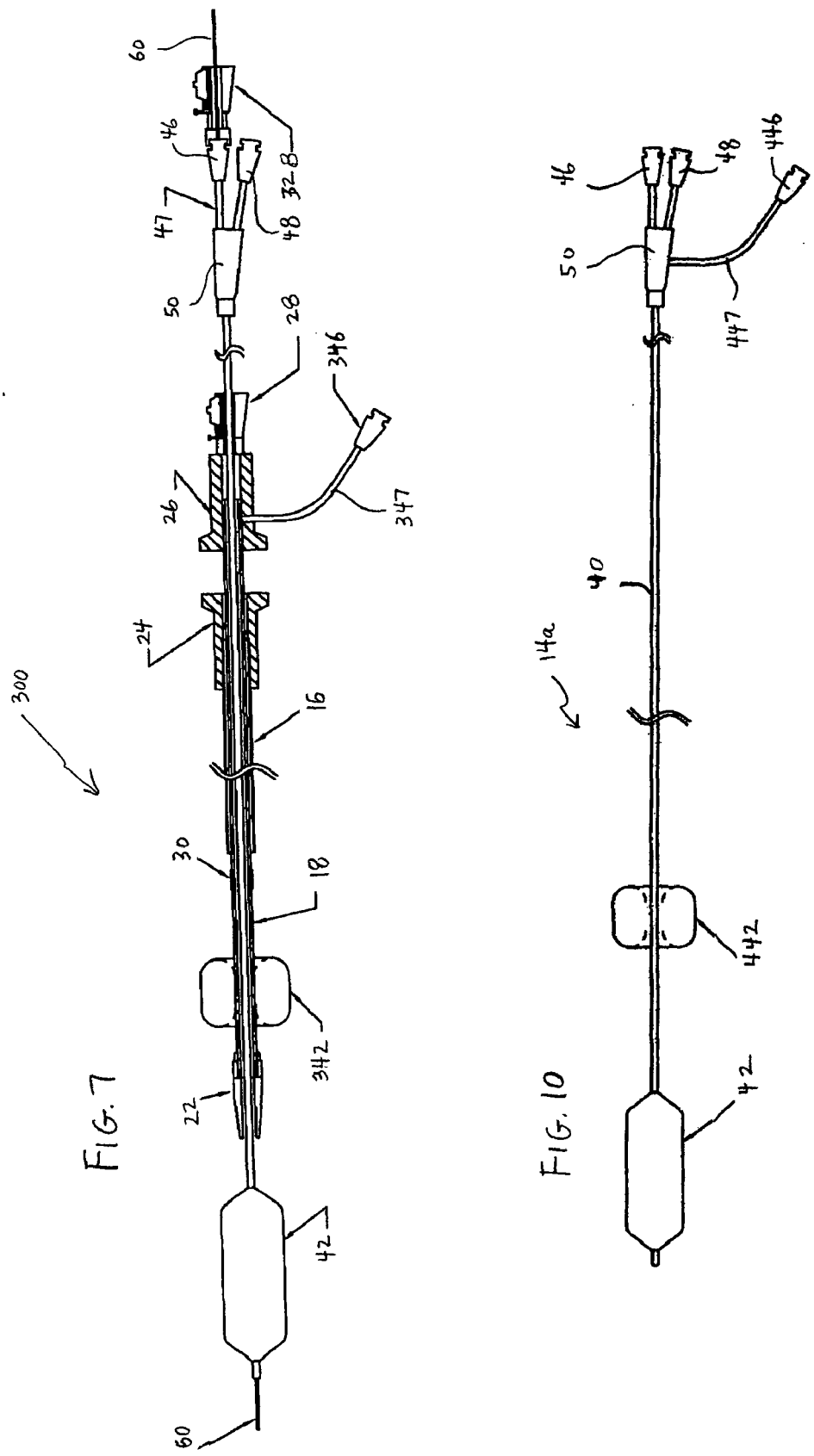

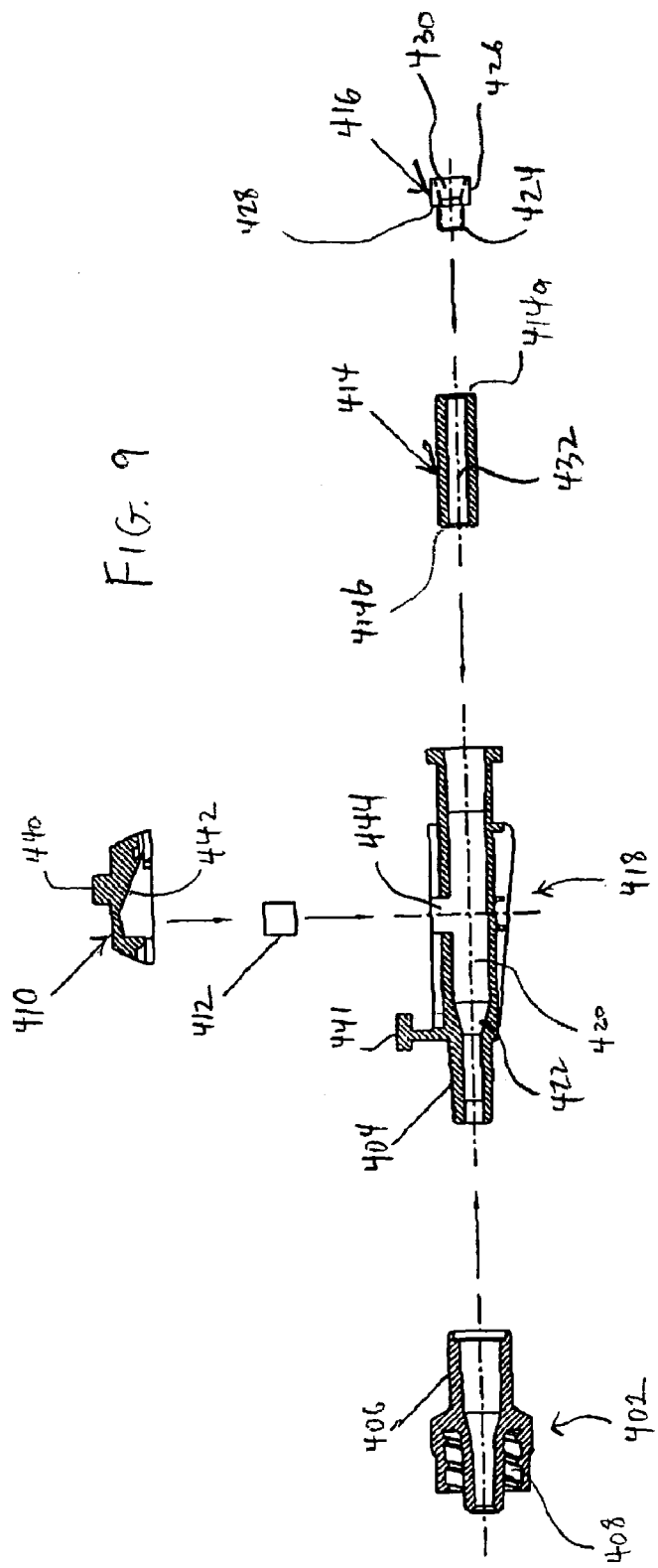

DILATATION AND STENT DELIVERY SYSTEM AND RELATED METHODS

BACKGROUND OF THE INVENTION

1. Field of the Invention

The present invention relates to a system for dilatation of a body passage and delivery of a stent into the body passage of a patient, and related methods of using such a system.

2. Description of Related Art

Stents are well-known endoprotheses. A conventional endoprosthetic stent includes a radially-expandable, tubular structure. The tubular structure can expand radially from a compact form for delivery to an expanded form for implantation. Radial expansion of the stent effects implantation into the tissue of a body passage wall being repaired, supported, or bridged. The body passage can include, for example, a body canal, blood vessel, duct, other passage, and the like.

A conventional endoprosthetic stent can be mechanically expansive or self-expansive. A conventional mechanically-expansive stent initially possesses a radially compact form. The stent is loaded onto a delivery system, such as a catheter. Typically, an expandable balloon is positioned in the tubular structure of the stent. After delivering the stent to the region of a body passage being repaired or bridged, the balloon is expanded, thereby implanting the stent onto the passage wall. To expand the stent, the balloon must be connected to a fluid source by means of a lumen or some other tubular structure.

A conventional self-expansive stent initially possesses a radially-expanded form. The stent is compressed radially as it is assembled onto a delivery system. Typically, an outer tubular structure retains the compressed stent until it is delivered to the region of a passage being repaired or bridged. The stent is then released from its compressed state and self-expands to implant onto the passage wall. An expandable balloon is not required to expand the stent. However, in cases where a stricture of the passage is difficult to repair or bridge, a physician may use a balloon to assist with expansion of the deployed stent.

Generally, when a balloon is used to assist with expansion of a self-expanding stent, the conventional stent delivery system is removed after the stent is successfully deployed. Then, either a separate single-use balloon catheter or a second delivery system having an expandable balloon is delivered to the site of the stent. In either event, a physician would be slowed by this process of removing the stent delivery system and delivering the balloon.

Conventional stent delivery systems generally include a minimal transverse dimension so that a distal end of the delivery system can be navigated through and along a patient's lumens, either in a percutaneous insertion procedure, through the working channel of an endoscope or laparoscope, or next to a scope. Often times, physicians use a delivery system in combination with a medical guide wire. Typically, in transluminal procedures, the physician directs a guide wire through narrow passages in a patient's body using a steering mechanism provided at a proximal end outside of the body. The physician monitors the travel and position of a distal end of the guide wire by a fluoroscope or other known method or device. Once the distal end of the guide wire reaches a desired position, the steering mechanism is removed and the delivery system is directed into the passage along the guide wire. Other procedures for directing catheters or similar devices into larger passages of the body, such as the esophagus, are also well known.

In some cases, it is desirable to dilate the body passage prior to deploying a stent in the passage, especially in the case of a stricture in the passage. In such a case, a balloon catheter is directed into the passage along the guide wire and the balloon is inflated to dilate the stricture in the body passage.

Thus, use of a conventional delivery system for a self-expanding stent in combination with a guide wire, a pre-deployment dilatation balloon, and a post-deployment expandable balloon, would require the following time-consuming procedures: delivery of the guide wire; delivery and activation of the pre-deployment balloon to dilate the passage; removal of the pre-deployment balloon; delivery of the stent deployment system and deployment of the stent; removal of the stent delivery system; delivery and activation of an expandable balloon device to assist in expansion of the stent; and removal of the expandable balloon device and guide wire. The repeated insertion and removal of delivery systems is cumbersome, prolongs the procedure, increases the trauma and risk to the patient, and increases costs.

SUMMARY OF THE INVENTION

To overcome the disadvantages of the prior art, and in accordance with the purposes of the invention, as embodied and broadly described herein, there is provided a dilatation and stent delivery system that includes a dilatation catheter having an expandable member on a distal end, and a stent delivery catheter configured to retain a stent and deliver the stent to a body passage. The stent delivery catheter defines a lumen sized to receive the dilatation catheter and permit movement of the dilatation catheter relative to the stent delivery catheter.

According to an embodiment, the stent delivery catheter includes a locking mechanism at a proximal end for selectively restricting movement of at least a portion of the stent delivery catheter relative to the dilatation catheter.

According to other embodiments, the stent delivery catheter includes an outer sheath, an inner shaft sized to be received in a lumen of the outer sheath, and a locking mechanism fixed to a proximal end of the inner shaft for selectively restricting movement of the inner shaft relative to the dilatation catheter. The locking mechanism is configured to selectively engage the dilatation catheter. The locking mechanism attaches to a proximal end of a handle at a proximal end of the inner shaft. The inner shaft terminates in the handle, and the locking mechanism defines a lumen to receive the dilatation catheter. According to further embodiments, the inner shaft includes a stent holder spaced from a distal end of the inner shaft and configured to retain the stent, the outer sheath moves relative to the inner shaft, and a first handle is at a proximal end of the outer sheath and a second handle is at the proximal end of the inner shaft.

According to still further embodiments, the expandable member is a balloon. The balloon may expand to a plurality of distinct diameters corresponding to known inflation pressures.

According to even further embodiments, the dilatation catheter defines an inflation lumen for passing inflation fluid to the expandable member and a guide wire lumen for accommodating a guide wire. A length of the dilatation catheter may be greater than a length of the stent delivery catheter.

According to other embodiments of the invention, the stent delivery catheter includes an outer sheath and an inner shaft sized to be received in a lumen of the outer sheath. A guide wire, hypotube, coil, or other like-structure may be placed within a lumen of the inner shaft and include a distal tip having a cross-sectional size at least as large as a cross-sectional size of the outer sheath.

Further embodiments include a second expandable member at a distal end of the dilatation and stent delivery system. The second expandable member may be located on a distal end of the stent delivery catheter or on a separate dilatation catheter. The expandable member of the dilatation catheter expands to a first diameter, the second expandable member expands to a second diameter, and the second diameter is larger than the first diameter.

According to another aspect, the invention includes a combination of a stent and a dilatation and stent delivery system. The stent may be a self-expanding stent.

According to a further aspect, the invention includes a method for implantation of a stent. The method includes delivering a stent delivery catheter proximate to a treatment site in a body passage, the stent delivery catheter retaining the stent; delivering a dilatation catheter proximate to the treatment site in the body passage, the dilatation catheter having an expandable member on a distal end; implanting the stent at the treatment site, while at least a portion of the dilatation catheter is positioned within a lumen of the stent delivery catheter; and expanding the expandable member to assist in expansion of the stent. According to an embodiment, the method further includes expanding the expandable member to dilate the treatment site of the body passage prior to implanting the stent. According to another embodiment, the stent is implanted while the dilatation catheter is positioned proximate the treatment site.

According to other embodiments, the expandable member is expanded to dilate the treatment site, while the stent delivery catheter is proximate the treatment site and while at least a portion of the dilatation catheter is positioned within the lumen of the stent delivery catheter. The expandable member may be expanded to assist in expansion of the stent, while the stent delivery catheter is proximate the treatment site and while at least a portion of the dilatation catheter is positioned within the lumen of the stent delivery catheter.

According to further embodiments, the dilatation catheter is delivered proximate to the treatment site at the same time as the stent delivery catheter is delivered proximate to the treatment site, the dilatation catheter reaches the treatment site prior to the stent delivery catheter reaching the treatment site, or the dilatation catheter is delivered proximate to the treatment site after delivery of the stent delivery catheter proximate to the treatment site.

According to still further embodiments, the method includes exposing the expandable member beyond a distal end of the stent delivery catheter prior to expanding the expandable member to dilate the treatment site of the body passage, and withdrawing the expandable member into the distal end of the stent delivery catheter prior to the stent implanting step and/or moving the distal end of the stent delivery catheter over the expandable member prior to the stent implanting step. The method also may include exposing the expandable member beyond a distal end of the stent delivery catheter prior to expanding the expandable member to assist in expansion of the stent.

According to additional embodiments, the method further includes restricting movement of the dilatation catheter relative to at least a portion of the stent delivery catheter. The stent delivery catheter includes an outer sheath, an inner shaft sized to be received in a lumen of the outer sheath, and a locking mechanism fixed to a proximal end of the inner shaft, and the restricting step includes actuating the locking mechanism to restrict movement of the inner shaft relative to the dilatation catheter. The restricting step may occur during the implanting step.

According to another embodiment, the step of expanding the expandable member to dilate the treatment site is performed prior to delivering the stent delivery catheter to the treatment site.

According to embodiments, the dilatation catheter includes a dilatation shaft and the expandable member is a balloon mounted on a distal end of the dilatation shaft, the stent delivery catheter includes an outer sheath and an inner shaft sized to be received in the outer sheath, and the inner shaft defines a lumen sized to receive the dilatation shaft and permit movement of the dilatation shaft relative to the stent delivery catheter. The expandable member may be inflatable.

According to further embodiments, the method further includes expanding a second expandable member to expand an end of the stent. The second expandable member may be located on a distal end of the stent delivery catheter. The expandable member on the distal end of the dilatation catheter is expanded to a first diameter and the second expandable member is expanded to a second diameter larger than the first diameter. The method may include expanding a second expandable member to expand only a portion of the stent.

According to another aspect of the invention, a method for implantation of a stent includes delivering a stent delivery catheter proximate to a treatment site in a body passage, the stent delivery catheter retaining the stent; delivering a dilatation catheter proximate to the treatment site in the body passage, the dilatation catheter having an expandable member on a distal end; implanting the stent at the treatment site, while movement of the dilatation catheter is restricted relative to at least a portion of the stent delivery catheter; and expanding the expandable member to assist in expansion of the stent.

BRIEF DESCRIPTION OF THE DRAWINGS

The accompanying drawings, which are incorporated in and constitute part of the specification, illustrate presently preferred embodiments of the invention and, together with the general description given above and detailed description of the preferred embodiments given below, serve to explain the principles of the invention.

FIG. 1 is a cross-sectional view of an embodiment of a dilatation and delivery system according to the invention;

FIG. 2 is a cross-sectional view of an embodiment of a stent delivery catheter of the delivery system of FIG. 1;

FIG. 3 is a plan view of an embodiment of a dilatation catheter of the delivery system of FIG. 1;

FIG. 4 is a cross-sectional view of the delivery system of FIG. 1, with an outer sheath retracted relative to an inner shaft to release a stent, according to an embodiment;

FIG. 5 is a cross-sectional view of another embodiment of a dilatation and delivery system according to the invention;

FIG. 6 is a cross-sectional view of a further embodiment of a dilatation and delivery system according to the invention;

FIG. 7 is a cross-sectional view of a still further embodiment of a dilatation and delivery system according to the invention;

FIG. 9 is an exploded cross-sectional view of the lock adapter of FIGS. 8B and 8C; and FIG. 10 is a plan view of an alternative embodiment of a dilatation catheter for use in a system according to the invention.

DESCRIPTION OF THE PREFERRED EMBODIMENTS

Figure 8A:
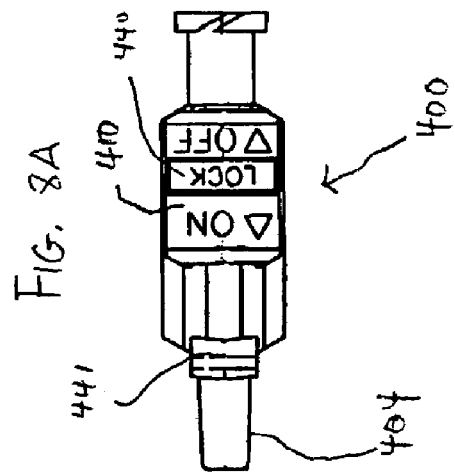
FIG. 8A is a top view of a lock portion of an embodiment of a lock adapter used in dilatation and delivery systems according to the invention.
Figure 8B:
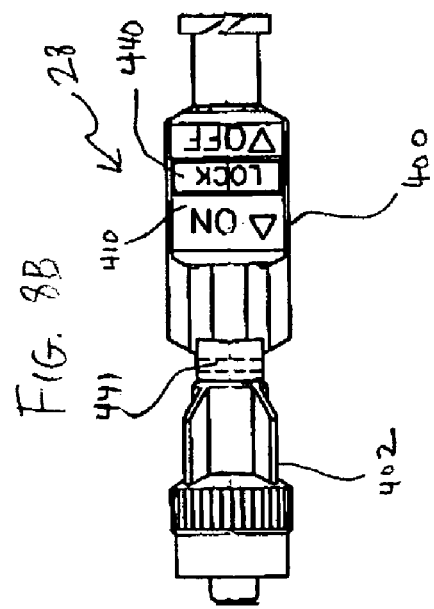
FIGS. 8B and 8C are respectively a top view and a side cross-sectional view of an embodiment of a lock adapter used in dilatation and delivery systems according to the invention.

Reference now will be made in detail to the present preferred embodiments of the invention, examples of which are illustrated in the accompanying drawings, in which like numerals designate like elements.

The present invention relates to a system for a less cumbersome, less time-consuming, and safer method for dilating a passageway in a body and implanting a stent in the passageway. According to embodiments to be described, the system includes a dilatation device having an expandable member, such as a balloon, on a distal end, and a stent delivery device that retains a stent and has a lumen that accommodates the dilatation device. The dilatation device may be moved independent of the stent delivery device. A locking mechanism may be provided at the proximal end to restrict movement of the dilatation device relative to at least a portion of the stent delivery device during suitable stages of the procedure, such as during stent implantation.

The dilatation and stent delivery devices may be delivered over a guide wire and may be delivered proximate to the treatment site either together or separately. Once delivered to the site, the dilatation and stent delivery devices each may remain proximate to the treatment site during the entire procedure, i.e. the dilatation device may remain proximate the site as the stent is delivered, and the stent delivery device may remain proximate the site during pre-dilatation of the passage and/or balloon assisted expansion of the stent. The dilatation and stent delivery devices therefore do not need to be removed during the procedure, decreasing the steps and time required of the procedure and the trauma to the patient.

The system and method of the present invention is suitable for use in any passageway of a body, including gastrointestinal passages, blood vessels, or other body lumens. The system and method may be applied in endoscopic procedures, such as procedures involving esophageal, biliary, pulmonary, urology, and colon stricture management.

FIG. 1 shows a dilatation and stent delivery system 10 according to an embodiment of the present invention. System 10 includes a stent delivery device, or catheter, 12 and a dilatation device, or catheter, 14. Catheters 12 and 14 are shown separately in FIGS. 2 and 3, respectively.

With reference to FIG. 2, stent delivery catheter 12 includes an outer member, or sheath, 16 and an inner member, or shaft, 18. Preferably, sheath 16 and shaft 18 are tubular shaped and relatively flexible to traverse tortuous anatomy. Sheath 16 defines an inner lumen that accommodates shaft 18 and through which shaft 18 moves axially relative to sheath 16. In a preferred embodiment, sheath 16 has an outer diameter of approximately 2.5-20 mm. Shaft 18 also defines a lumen 20 therein that has a size sufficient to accommodate dilatation catheter 14 or other devices, such as other dilatation devices, guide devices, or other therapeutic or diagnostic devices, as desired. Catheter 14 moves axially through lumen 20 relative to shaft 18 and sheath 16. In a preferred embodiment, shaft 18 has an outer diameter of approximately 2-19 mm and defines a lumen 20 having a diameter of approximately 1-18 mm.

Preferably, a length of dilatation catheter 14 is greater than a length of stent delivery catheter 12. For example, for an operation within the esophagus of a patient, dilatation catheter 14 may have a length of about 140 cm to about 200 cm, and stent delivery catheter may have a length of about 100 cm to about 130 cm. Other catheter lengths are within the scope of the invention.

A distal tip 22 connects to the distal end of shaft 18. Tip 22 is tapered and has a conical shape. Tip 22 is made of a material that will not damage tissue as stent delivery catheter 12 inserts and travels through a body passage. Tip 22 has a reduced diameter proximal portion 23, as most clearly shown in FIG. 4, that receives the distal end of sheath 16 and acts as a seat for sheath 16 when sheath 16 is in its distal most position relative to shaft 18. In this embodiment, the diameter of tip 22 at its largest point approximates the outer diameter of sheath 16.

At its proximal end, stent delivery catheter 12 includes an inner sheath handle 26 that is fixedly connected to the proximal end of shaft 18. Catheter 12 also includes a handle 24 fixedly connected to the proximal end of outer sheath 16. Each of handles 24,26 may be any suitable handle known in the art for moving inner shaft 18 and outer sheath 16 relative to one another.

Handle 26 includes a lock mechanism, or adapter, 28 for releasably locking dilatation catheter 14 relative to inner shaft 18, as will be described in more detail below. Lock adapter 28 selectively restricts movement of at least a portion of stent delivery catheter 12 relative to dilatation catheter 14. More specifically, lock adapter 28 selectively engages shaft 40 and thereby restricts movement of shaft 40 relative to inner shaft 18.

Lock adapter 28 is fixed to a proximal end of handle 26 and defines a lumen to receive dilatation catheter 14. An embodiment of lock adapter 28 is shown in FIGS. 8A-8C and 9. Lock adapter 28 includes a lock portion 400 and a luer adapter 402. A distal nose portion 404 of lock portion 400 frictionally fits within a proximal end 406 of adapter 402. An internally-threaded distal end 408 of adapter 402 engages the proximal end of handle 26 to connect lock adapter 28 to handle 26. Alternatively, a locking mechanism may be incorporated into the proximal handle.

Figure 8C:
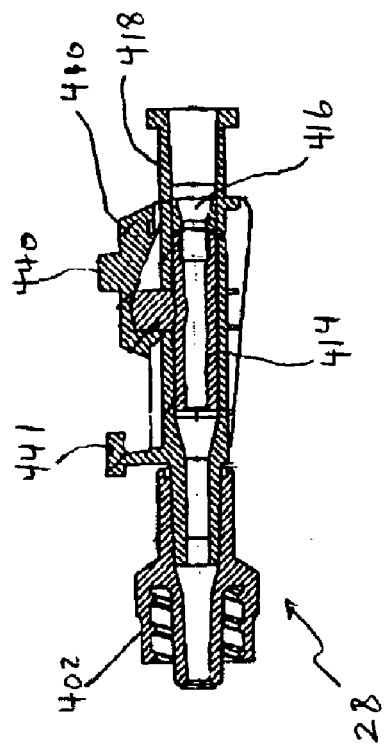

As shown in FIGS. 8C and 9, lock portion 400 includes five parts: a button 410; a pressure member 412; a tube 414; a tube holder 416; and a main casing 418 that receives the other four parts. Main casing defines a central, longitudinal lumen 420 that accommodates tube 414 and tube holder 416. A distal end 414b of tube 414 rests against an angled stop surface 422 of casing 418. A proximal end 414a of tube 414 receives a distal extension 424 of tube holder 416. A proximal portion 426 of tube holder 416 has an outer diameter closely matching the inner diameter at the proximal end of lumen 420 of casing 418, so that holder 416 frictionally fits within casing 418. The proximal end 414a of tube 414 rests against a stop 428 formed between extension 424 and portion 426. A lumen 430 of holder 416, a lumen 432 of tube 414, and lumen 420 of casing 418 are configured to receive a medical device, such as a guide wire, balloon catheter, or any other desired device.

Button 410 has a raised finger trigger 440 on a top surface. Casing 418 includes suitable structure, such as groves; to receive complementary structure on a bottom of button 410, such as ridges, to permit button 410 to slide longitudinally along casing 418. Lock adapter 28 is a linear locking system in that, pressing finger trigger 440 forward by a user's thumb, for example, sets lock adapter 28 in the "on," or locked, position. Stop 441 of casing 418 limits forward movement of button 410. Movement of finger trigger 440 in the proximal direction sets lock adapter 28 in the "off," or unlocked position.

Button 410 includes a ramped undersurface 442 which slides against the top of pressure member 412. Member 412 rests between undersurface 442 and tube 414 within a passage 444 of casing 418. Tbe 414, and optionally member 412, is preferably made of a resilient material so that, as button 410 is moved forward (i.e., distally), the pressing of undersurface 442 against member 412 forces member 412 against tube 414. This causes a portion of tube 414 to deflect inwardly and against a medical device (such as dilatation catheter 14), thus locking the medical device relative to lock adapter 28.

Any other structure associated with stent delivery catheter 12 or dilatation catheter 14 that is suitable for restricting movement of all or portions of the catheters relative to one another may be used. For example, various commercially available locking mechanisms may be used, including a male touhy borst with a spin lock available from Qosina (Part No. 80345).

A stent holder 30 is located on an outer surface of shaft 18 near its distal end, as shown in FIG. 4. Stent holder 30 may be a holding sleeve coaxially mounted about the inner shaft 18 and sized and configured such that a self-expanding stent can be placed around it. The holding sleeve can retain the positioning of the stent during delivery by cooperating with the outer sheath 16 to prevent axial movement of the stent. In this way, the stent may be reconstrained during delivery if necessary because, for example, initial stent placement is not accurate.

Stents suitable for use in combination with this invention include bioabsorbable and/or polymer stents, such as stents made of bioabsorbable poly-1-lactide filaments braided in a tubular mesh configuration. Stents made of nitinol, stents with coverings to resist tissue ingrowth for example, and any other suitable, biocompatible stent also may be used. One or both ends of the stent may be flared upon expansion to assist in anchoring the stent in place. The invention in its broadest sense is not limited by the shape, size, composition, or type of the self-expanding stent. Moreover, the invention includes in its broadest sense expandable stents, such as balloon-expandable stents.

With reference to FIG. 3, dilatation catheter 14 includes an elongate member, or shaft, 40 that is preferably tubular and relatively flexible to traverse tortuous anatomy. Shaft 40 preferably includes two lumens to accommodate the guide wire and inflation media. A first lumen communicates with a port 46 that accepts a guide wire 60. A second lumen communicates with a port 48 to receive and pass inflation fluid from the proximal end to an inflation device 42 at the distal end. Port 48 connects to any suitable inflation device known in the art, such as a syringe. The inflation medium may be any suitable fluid known in the art, such as air, saline, or a radiographic dye suitable for endoscopic visualization. Ports 46, 48 may be luer adapters or any other suitable like device known in the art. Tubes 47, 49 are affixed to and communicate with ports 46, 48 and lead to the guide wire lumen and inflation lumen, respectively. A connector 50 provides the connection of ports 46, 48 to the remainder of dilatation catheter shaft 40. Connector 50 is a molded Y-connector. Any other suitable connector known in the art may be used. Shaft 40 also includes an atraumatic distal tip 44 that includes a lumen therein and a hole at its distal end, permitting passage of guide wire 60 through the distal end of dilatation catheter 14. When catheters 12 and 14 are in their relative positions as shown in FIG. 1, tip 44 provides a reduction in the profile of the tip section from the profile of tip 22. It is contemplated that embodiments of catheter 12 will not include a distal tip 22, in which case distal tip 44 exposed from the distal end of catheter 12 creates the atraumatic distal tip for the system.

Inflation device 42 is preferably a balloon coaxially mounted about shaft 40. A port or hole in shaft 40 (not shown in the Figures) will permit inflation fluid to pass from the inflation lumen of shaft 40 to balloon 42. In an embodiment, balloon 42 may be inflatable to a plurality of distinct, pressure-controlled diameters. Such a multi-stage dilatation catheter is sold commercially by Boston Scientific Corporation under the name CRE™ Wireguided Balloon Dilator. The CRE™ Wireguided Balloon Dilator includes a balloon that is inflatable to three distinct diameters at three separate pressures, with little or no waisting of the balloon and with a high degree of radial force at any given pressure. For example, at pressures of 3, 5, and 8 atmospheres, the balloon increases to diameters of 10, 11, and 12 mm, respectively. Other balloon dilatation catheters may be used, including those with balloons that do not inflate to distinct diameters at known pressures.

FIG. 1 shows shaft 40 of dilatation catheter 14 inserted within lumen 20 of stent delivery catheter 12. In FIG. 1, outer sheath 16 is in its distal most position relative to inner shaft 18, and substantially all of balloon 42 is within lumen 20 of catheter 12. Atraumatic tip 44 is exposed from the distal end of catheter 12. This relative positioning of catheters 12 and 14, and sheath 16 and shaft 18, is suitable for inserting delivery system 10 over guide wire 60 and passing system 10 through a patient's tortuous anatomy to a site of interest in, for example, an esophagus. In this position, lock adapter 28 may be actuated to engage shaft 40 to restrict movement of shaft 40 relative to shaft 18. As alternatives to inserting catheters 12 and 14 together in the locked, relative positions shown in FIG. 1, and as will be described, catheters 12 and 14 may be inserted separately to the treatment site, inserted together in different relative positions, for example with balloon 42 extending from the distal end of delivery catheter 12, or inserted together without actuating lock adapter 28 to restrict relative movement.

The invention includes a method for dilatation and for delivery of a stent that uses a delivery system having a stent delivery catheter and a dilatation catheter. According to an embodiment of the invention, the delivery system is passed along a conventional guide wire to the area of the anatomical passage to be treated. In other embodiments, the delivery system may be passed through an endoscope or along an endoscope to the treatment site.

In embodiments using a guide wire, once a guide wire has been inserted into the patient and traversed an anatomical passage to the area to be treated through any known, conventional method, delivery system 10 may be inserted over the wire to the treatment site. This may be accomplished in a number of ways. For example, the user may first insert stent delivery catheter 12 over the wire to the treatment site, followed by dilatation catheter 14 over the wire and through stent delivery catheter 12. As an alternative, stent delivery catheter 12 and dilatation device 14 may be inserted together as a unit in their relative positions shown in FIG. 1. Inserting the catheters together advantageously lessens the number of steps in the procedure. During insertion, lock adapter 28 may be actuated to restrict relative movement of the catheters. Adapter 28 may restrict movement during insertion with tip 44 exposed from the end of catheter 12, as shown in FIG. 1. As an even further alternative, catheters 12 and 14 may be inserted together in relative positions different than that shown in FIG. 1, for example with balloon 42 extending from the distal end of delivery catheter 12, in a locked or unlocked state.

Once delivery system 10 is positioned proximate the treatment site, dilatation catheter 14 is extended distally relative to stent delivery catheter 12 to expose balloon 42 from the distal end of catheter 12. To do so, the user first must ensure that lock adapter 28 is in the unlocked position so that shaft 40 may move axially relative to shaft 18. Then, the user either pushes catheter 14 distally or pulls catheter 12 proximally until balloon 42 is exposed. The user then positions balloon 42 in the body passage at the site to be dilated.

Suitable visualization techniques known to those skilled in the art may be used to aid in positioning catheters 12 and 14 and their components. For example, radiopaque markers may be fixed at appropriate positions along the delivery system 10 and fluoroscopic visualization may be used. As another example, one or both catheters may be made radiopaque by mixing a radiopaque compound such as tungsten or barium sulfate to the polymer from which the catheter is manufactured.

Once balloon 42 is positioned, suitable inflation media is inserted through a lumen of dilatation catheter 14 to balloon 42 to inflate balloon and dilate the treatment site. If a multi-stage dilatation catheter such as a CRE™ Wireguided Balloon Dilator is used, the balloon may be inflated to a distinct diameter at a known pressure. In certain embodiments of the method, the treatment site may not require dilatation prior to stent deployment.

After suitable dilatation of the passage, if such dilatation is required or desired, the user deflates balloon 42 and moves dilatation catheter 14 in a proximal direction relative to delivery catheter 12, by either pulling catheter 14 into catheter 12 or pushing catheter 12 over catheter 14. This position is shown in FIG. 1. The user then may place lock adapter 28 in the locked position so that shaft 40 is fixed relative to shaft 18.

The user then may reposition delivery system 10 as needed, for stent holder 30 and its held stent to be positioned at the treatment site. The user may either retract balloon 42 into catheter 12, advance catheter 12 over balloon 42, or leave balloon 42 exposed. Once again, such positioning may be performed through any suitable visualization techniques known to those skilled in the art.

Once the stent is in its proper position, the user pulls on handle 24 to retract sheath 16 relative to shaft 18, until stent holder 30 and its held stent are exposed. This will release the stent and allow the stent to self-expand within the body passage. The user thereafter may move handle 24 distally to reposition sheath 16 in the position shown in FIG. 1, or retract handle 26 to avoid the possibility that handle 24 will contact the delivered stent.

If additional expansion of the stent is needed, the user then may reposition system 10 so that balloon 42 is positioned within the stent. If balloon 42 is not already exposed from the distal end of catheter 12, the user unlocks lock adapter 28 so that shaft 40 may move relative to shaft 18. The user then retracts stent delivery catheter 12 relative to dilatation catheter 14 by pulling catheter 12 in the proximal direction. The user retracts catheter 12 until balloon 42 is exposed at the distal end. Suitable inflation media then is inserted through a lumen of dilatation catheter 14 to balloon 42 to inflate balloon 42 and assist in expanding the stent and further dilating the body passage. If a multi-stage dilatation catheter such as a CRE™ Wireguided Balloon Dilator is used, the balloon may be inflated to a distinct diameter at a known pressure.

Once the stent is expanded to the desired diameter, balloon 42 may be deflated and, if desired, repositioned within an end of the stent to expand a flare at that end. Once balloon is properly positioned, suitable inflation media then is inserted through a lumen of dilatation catheter 14 to balloon 42 to inflate balloon 42 and expand the flared stent end. If a multi-stage dilatation catheter such as a CRE™ Wireguided Balloon Dilator is used, the balloon may be inflated to a distinct diameter at a known pressure.

Once the stent end is expanded, balloon 42 may be deflated. The user then may remove delivery system 10, including stent delivery catheter 12 and dilatation catheter 14, and guide wire 60 from the patient's body.

FIG. 5 shows a stent delivery system 100 according to another embodiment of the present invention. This embodiment differs from that shown in FIGS. 1-4 primarily in the placement of a distal tip relative to the delivery system. The reference numerals used in connection with FIGS. 1-4 designate like elements in the embodiment shown in FIG. 5. In this embodiment, a distal tip 122 is fixedly connected at its proximal end to a distal end of a hypotube 124. As an alternative to the arrangement shown in FIG. 5, hypotube 124 may be a coil for increased flexibility. The coil may be metal and also may include a biocompatible covering. Hypotube 124 extends through and may move relative to a lumen of dilatation catheter 14. Hypotube 124 has a length greater than that of dilatation catheter and has a proximal end that extends out of the proximal end of dilatation catheter 14. Distal tip 122 may be manipulated by a user at that proximal end of tube 124. At least a portion of distal tip 122 has a cross-sectional size at least as large as a cross-sectional size of outer sheath 16. Distal tip 122 therefore can stop forward relative movement of sheath 16. A guide wire 60 may extend through the lumen of hypotube 124 and a central lumen of distal tip 122, as shown in FIG. 5.

The embodiment of delivery system 100 shown in FIG. 5 is used in a similar fashion as that described in connection with the embodiment of FIGS. 1-4. The main differences include delivery of hypotube 124 over wire 60 once wire 60 reaches a treatment site. Distal tip 122 preferably extends distally of the treatment site so that balloon 42 and stent holder 30 may reach the site. Catheters 12 and 14 may be inserted with hypotube 124 over wire 60, or catheters 12 and 14 may be inserted over hypotube 124 after hypotube 124 reaches a treatment site. The remaining method steps when using system 100 are the same as or substantially the same as the steps described above in connection with other embodiments.

FIG. 6 shows a stent delivery system 200 according to another embodiment of the present invention. This embodiment differs from that shown in FIGS. 1-4 and 5 primarily in the placement of a distal tip relative to the delivery system. The reference numerals used in connection with FIGS. 1-4 and 5 designate like elements in the embodiment shown in FIG. 6. In this embodiment, a distal tip 222 is directly connected at its proximal end to the tip of the dilatation catheter. At least a portion of distal tip 222 has a cross-sectional size at least as large as a cross-sectional size of outer sheath 16 to stop forward relative movement of sheath 16. Distal tip 222 has a central lumen to accept a guide wire 60 that moves relative to tip 222. The embodiment of delivery system 200 shown in FIG. 6 is used in a similar fashion as that described in connection with the embodiment shown in FIGS. 1-4.

In a further embodiment of the present invention, a second expandable member, or balloon, may be incorporated into the system. In one embodiment, the additional balloon may be placed on the stent delivery catheter, preferably distal to the stent holder. The additional balloon may have different characteristics than the dilatation balloon, for example expandable to a different and larger diameter. The additional balloon may be used, for example, to expand the ends of a flared stent.

FIG. 7 shows an embodiment of a dilatation and delivery system 300 that incorporates a second expandable member. The reference numerals used in connection with the above-described Figures designate like elements in the embodiment shown in FIG. 7. The differences of the FIG. 7 embodiment will be described. The second expandable member is a balloon 342 on stent delivery catheter 12, and specifically inner shaft 18. Balloon 342 is positioned distal to stent holder 30. In this embodiment, balloon 342 expands to a larger diameter than balloon 42, as shown in FIG. 7.

At the proximal end of the delivery system 300, handle 26 that attaches to inner shaft 18 includes a side passage that receives a tube 347. Tube 347 has a port 346 at its proximal end. Port 346 is configured to connect to any suitable inflation source (not shown) to supply inflation media through inner shaft 18 to balloon 342.

Balloon 342 may be used, for example, to expand the ends of a flared stent at areas where no stricture exists. After balloon 42 aids in expansion of the stent to the desired diameter under a stricture and balloon 42 subsequently is deflated, balloon 342 may be positioned within an end of the stent to expand a flare at that end. Once balloon 342 is properly positioned, suitable inflation media is inserted through port 346, tube 347, and a lumen of inner shaft 18 to balloon 342 to inflate balloon 342 and expand the flared stent end. Each end of a stent may be flared in this way.

Also at its proximal end, delivery system 300 includes a second lock adapter 328 for restricting movement of guide wire 60 relative to dilatation catheter 14. Such a lock adapter may be used in the systems described above as well. Lock adapter 328 may include the same or similar structural components as the lock adapter shown and described in connection with FIGS. 8A-8C and 9, and therefore operate in a like fashion. Alternatively, lock adapter 328 may be any suitable locking mechanism known in the art.

As an alternative embodiment to the system shown in FIG. 7, an additional balloon may be placed on the dilatation catheter. This embodiment is shown FIG. 10. Dilatation catheter 14a includes a balloon 442 proximate dilatation balloon 42 and proximal to balloon 42. As an alternative, balloon 442 could be distal to balloon 42. With this arrangement, an additional inflation port 446 and tube 447 corresponding to balloon 442 connects at the proximal end of catheter 14a to connector 50. Inflation media may be supplied through port 446 and through an additional lumen (not shown) of catheter 14a to balloon 442.

Balloon 442 may be used, for example, to expand the ends of a flared stent at areas where no stricture exists. After balloon 42 aids in expansion of the stent to the desired diameter under a stricture and balloon 42 subsequently is deflated, balloon 442 may be positioned within an end of the stent to expand a flare at that end. Once balloon 442 is properly positioned, suitable inflation media is inserted through port 446, tube 447, and a lumen of inner shaft 18 to balloon 442 to inflate balloon 442 and expand the flared stent end. Each end of a stent may be flared in this way.

While this invention has been described with specific embodiments thereof, it is evident that many alternatives, modifications, and variations will be apparent to those skilled in the art. Accordingly, the preferred embodiments of the invention as set forth herein are intended to be illustrative, not limiting. Various changes may be made without departing from the spirit and scope of the invention.

We claim:

1. A dilatation and stent delivery system, the system comprising:
    a dilatation catheter, the dilatation catheter having an expandable member; and
    a stent delivery catheter, the stent delivery catheter comprising:
        an inner shaft, the inner shaft comprising a stent retaining region, the inner shaft defining a lumen sized to receive the dilatation catheter and to permit movement of the dilatation catheter relative to the stent delivery catheter,
        an outer sheath, the outer sheath having a non-retracted state and a retracted state, the outer sheath comprising a distal end, the distal end of sheath being disposed over the stent retaining region of the inner shaft when the outer sheath is in the non-retracted state, the distal end of the outer sheath being proximal to the stent retaining region when the outer sheath is in the retracted state.

2. The system of claim 1, wherein the stent delivery catheter includes a locking mechanism at a proximal end for selectively restricting movement of at least a portion of the stent delivery catheter relative to the dilatation catheter.

3. The system of claim 1, wherein the stent delivery catheter further includes a locking mechanism fixed to a proximal end of the inner shaft for selectively restricting movement of the inner shaft relative to the dilatation catheter.

4. The system of claim 3, wherein the locking mechanism is configured to selectively engage the dilatation catheter.

5. The system of claim 3, further comprising a handle at a proximal end of the inner shaft, wherein the locking mechanism is attached to a proximal end of the handle.

6. The system of claim 5, wherein the inner shaft terminates in the handle, and the locking mechanism defines a lumen to receive the dilatation catheter.

7. The system of claim 3, the stent delivery catheter further comprising a stent holder configured to retain a stent on the stent retaining region of the inner shaft.

8. The system of claim 3, further comprising a first handle at a proximal end of the outer sheath and a second handle at the proximal end of the inner shaft.

9. The system of claim 1, wherein the expandable member is a balloon.

10. The system of claim 9, wherein the balloon expands to a plurality of distinct diameters corresponding to known inflation pressures.

11. The system of claim 1, wherein the dilatation catheter defines an inflation lumen for passing inflation fluid to the expandable member and a guide wire lumen for accommodating a guide wire.

12. The system of claim 1, wherein a length of the dilatation catheter is greater than a length of the stent delivery catheter.

13. The system of claim 1, wherein the dilatation catheter includes a distal tip a portion of which has a cross-sectional size at least as large as a cross-sectional size of the outer sheath.

14. The system of claim 1, further comprising a second expandable member at a distal end of the dilatation and stent delivery system.

15. The system of claim 14, wherein the second expandable member is located on a distal end of the stent delivery catheter.

16. The system of claim 14, wherein the second expandable member is located on the distal end of the dilatation catheter.

17. The system of claim 14, wherein the expandable member of the dilatation catheter expands to a first diameter, the second expandable member expands to a second diameter, and the second diameter is larger than the first diameter.

18. The system of claim 1, wherein the stent delivery catheter further comprises a stent holder configured to retain a stent on the stent retaining region of the inner shaft.

19. The system of claim 1, further comprising a stent disposed about the stent retaining region of the inner shaft.

20. The system of claim 1, wherein a distal end of the inner shaft is not fixedly coupled to the outer sheath.

21. The system of claim 1, wherein the inner shaft is extendable from and retractable into a distal end of the lumen of the outer sheath.

22. The system of claim 21, wherein the stent delivery catheter further includes a distal tip, the distal tip including a reduced diameter proximal portion for receiving a distal portion of the outer sheath and thereby acting as a seat when the outer sheath is in its distal most position relative to the inner shaft.

23. The system of claim 1, wherein the expandable member is capable of expanding to a plurality of distinct maximum diameters corresponding to known inflation pressures.

24. The system of claim 1, wherein the inner shaft is configured to slide along an inner surface of the outer sheath.

25. In combination, a stent and a dilatation and stent delivery system, the combination comprising:
 a stent;
 a dilatation catheter, the dilatation catheter having a balloon; and
 a stent delivery catheter, the stent delivery catheter comprising:
  an inner shaft, the inner shaft comprising a stent retaining region, the stent disposed about the stent retaining region; and
  a tip, the tip being tubular and engaged to a distal end of the inner shaft; the inner shaft and tip defining a lumen sized to receive the dilatation catheter and permit movement of the dilatation catheter relative to the stent delivery catheter.

26. The combination of claim 25, wherein the stent is a self-expanding stent.

27. The combination of claim 25, wherein the stent delivery catheter further comprises a sheath, the sheath having a non-retracted state and a retracted state, the sheath comprising a distal end, the distal end of the sheath being disposed on a proximal end of the tip and over the stent when the sheath is in the non-retracted state, and the distal end of the sheath being proximal to the stent retaining region when the sheath is in the retracted state.

* * * * *